United States Patent [19]

Schulte-Elte et al.

[11] 4,411,829

[45] Oct. 25, 1983

[54] PERFUMING INGREDIENT

[75] Inventors: Karl H. Schulte-Elte, Onex; Dietrich Kastner, Givrins, both of Switzerland

[73] Assignee: Firmenich SA, Switzerland

[21] Appl. No.: 331,013

[22] Filed: Dec. 15, 1981

[30] Foreign Application Priority Data

Jan. 13, 1981 [CH] Switzerland .......................... 177/81

[51] Int. Cl.[3] .......................... A61K 7/46; C11B 9/00

[52] U.S. Cl. .............................................. 252/522 R

[58] Field of Search .................................. 252/522 R

[56] References Cited

U.S. PATENT DOCUMENTS

| | | | |
|---|---|---|---|
| 4,006,108 | 2/1977 | Ochsner et al. | 252/522 R |
| 4,028,278 | 6/1977 | Buchi et al. | 252/522 R |
| 4,113,663 | 9/1978 | Schenk | 252/522 R |
| 4,144,199 | 3/1979 | Wille et al. | 252/522 R |
| 4,198,309 | 4/1980 | Mookherjie et al. | 252/522 R X |
| 4,324,704 | 4/1982 | Trenkle et al. | 252/522 R |

OTHER PUBLICATIONS

Arctander, Perfume and Flavor Chemicals, Steffen Arctander, N.J. vol. 1, #1198 (1969).

*Primary Examiner*—Helen M. S. Sneed
*Attorney, Agent, or Firm*—Pennie & Edmonds

[57] ABSTRACT

Methyl 2,6,6-trimethyl-cyclohex-2-en-1-yl carboxylate is a useful perfuming ingredient, especially for the reproduction of fruity, floral and fresh odor notes.

7 Claims, No Drawings

PERFUMING INGREDIENT

SUMMARY OF THE INVENTION

The invention refers to a method for modifying, enhancing or improving the odour properties of perfumes or perfumed articles, which comprises adding thereto a small but olfactively effective amount of methyl 2,6,6-trimethyl-cyclohex-2-en--yl carboxylate.

The invention more specifically refers to a method as defined hereinabove wherein said methyl 2,6,6-trimethyl-cyclohex-2-en-1-yl carboxylate is used either alone or in combination with at least one additional perfuming ingredient, selected from the group consisting of α-damascone, β-damascone, γ-damascone, δ-damascone, ε-damascone, α-damascenone, β-damascenone, γ-damascenone and δ-damascenone.

The invention also refers to perfume compositions as well as perfumed articles containing methyl 2,6,6-trimethyl-cyclohex-2-en-1-yl carboxylate as olfactively active ingredient.

BACKGROUND OF THE INVENTION

Methyl 2,6,6-trimethyl-cyclohex-2-en-1-yl carboxylate, having the formula

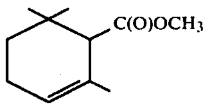

(I)

also defined as methyl α-cyclogeranate is a known compound [see e.g. Helv. Chim. Acta 42, 2597 (1959)]. Up to now, however, its olfactive properties have remained unrecognized in the art.

Among the great variety of synthetic compounds presently at the disposal of perfumers, there appears to be several alicyclic ester derivatives analogous or homologous to compound (I). Said ester derivatives are summarized hereinafter.

| Alicyclic esters | Odour description | Reference |
|---|---|---|
| 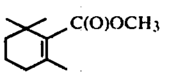 | no odour decsription | Helv. Chim. Acta 42,2597 (1959) |
| 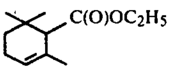 | camphoraceous, woody, flat, medicinal side-note | U.S. Pat. No. 4,113,663 |
| 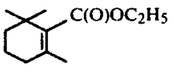 | refreshing, oily-green, vegetable, apple-like | Arctander[1] (1198) |
| 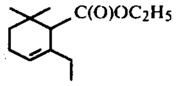 | diffusive rose note, honey, spicy, fruity, berry-like note | U.S. Pat. No. 4,113,663 |
| 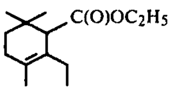 | slightly fruity and tobacco-like notes, eucalyptus | U.S. Pat. No. 4 006 108 |
| 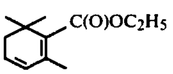 | general fruity, but not apple-like | U.S. Pat. No. 4 144 199 |
| + α and γ-isomers | | |

[1] S. Arctander, Perfume and Flavor Chemicals, Montclair N.J. 1969 (section no.)

From the above discussed state of the art one can deduct that higher homologues of methyl 2,6,6-trimethyl-cyclohex-2-en-1-yl carboxylate (I) are the only compounds presenting an interest for the perfumery. These higher homologues are more specifically ethyl ester derivatives having an ethyl group at position 2 of the six membered ring, as well as compounds possessing an additional methyl group at position 3, and isomeric mixtures of corresponding doubly unsaturated derivatives, ethyl α-, β- and γ-safranates more precisely.

Lower homologues such as methyl β-cyclogeranate and compound (I), however, never retained the perfumer's attention.

In contradiction with the above, we have surprisingly found that methyl 2,6,6-trimethyl-cyclohex-2-en-1-yl carboxylate (I) presented a great interest for the perfumery and that it could advantageously be used as perfuming ingredient.

PREFERRED EMBODIMENTS OF THE INVENTION

Methyl 2,6,6-trimethyl-cyclohex-2-en-1-yl carboxylate (I) exhibits an original odour note at the same time fruity and floral and also characterized by fresh nuances of citrus type. Surprisingly, these odour characters are particularly well developed when said compound is used in a rather diluted state, for instance in the form of 10, 5 or even 1% solutions.

In view of its interesting odour properties, compound (I) can be used advantageously for perfuming various products such as e.g. soaps, powder or liquid detergents, cosmetic preparations or household materials. It can also be used in fine perfumery, especially for the preparation of perfume compositions e.g. of fruity, flowery, rose, woody, spicy, chypre or citrus type.

For the preparation of perfume compositions, interesting effects can be achieved by making use of compound (I) in proportions preferably comprised between about 0.1 and 5 or even 10% (by weight) of the weight of the considered composition. Proportions higher than 10% can also be used, especially for the preparation of perfume bases or "coeurs". Proportions lower than 0.1%, for example of the order of about 0.05% (by weight) are preferably used for perfuming products such as soaps, detergents or cosmetic preparations.

Another embodiment of the invention consists in using methyl 2,6,6-trimethyl-cyclohex-2-en-1-yl carboxylate (I) in combination with at least one additional perfuming ingredient, a diluent or a solvent, more specifically in combination with at least one ingredient selected from the very important family of damascones and damascenones. These latter perfume ingredients are particularly well appreciated in the art, in fine perfumery as well as for perfuming technical products: they develop a remarkably radiant rosy and woody note, as well as in certain cases a fruity, apple-like or minty tonality.

We have summarized in the table hereinafter all the members of the series which can be put at the disposal of the perfumers.

| Compound | Name | Reference[1] |
|---|---|---|
| 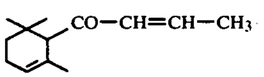  | α-Damascone[2] | CH 509,399 |
| 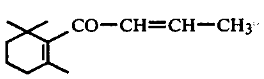  | β-Damascone[2] | CH 509,399 |
| 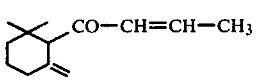  | γ-Damascone | CH 520,767 |
| 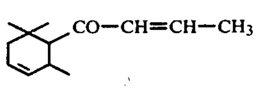  | δ-Damascone | CH 566,112 |
| 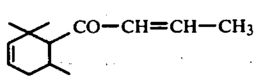  | ε-Damascone | CH 566,112 |
| 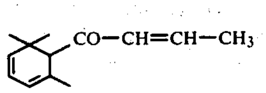  | α-Damascenone | CH 562,316 |
| 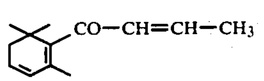  | β-Damascenone[3] | CH 509,399 |
| 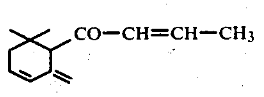  | γ-Damascenone | CH 562,316 |
| 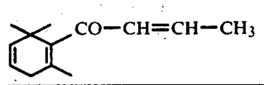  | δ-Damascenone | CH 562,316 |

(1)all the cited patents (assignee: FIRMENICH SA, Geneva/Switzerland) refer to the use of the said compounds as perfume ingredients.
(2)DORINONE ® (Origin: FIRMENICH SA, Geneva/Switzerland)
(3)DORICENONE ® (Origin: FIRMENICH SA, Geneva/Switzerland)

More particularly, we have discovered that said damascones or damascenones, when combined with methyl 2,6,6-trimethyl-cyclohex-2-en-1-yl carboxylate (I), developed a richer and rounder odour note. Said combinations, moreover, possess a remarkably lower threshold value than that of each of the individual constituents: in this particular case, we may speak of synergism.

In order to achieve these remarkable olfactive effects, the proportions of compound (I) and said damascones and/or damascenones can vary within large values, preferably from about 20:1 to 1:20 (parts by weight).

Methyl 2,6,6-trimethyl-cyclohex-2-en-1-yl carboxylate (I) can be easily prepared according to methods already published in the scientific literature, for instance by esterifying α-cyclogeranic acid or cyclyzing methyl geranate [see e.g. Helv. Chim. Acta 42, 2597 (1959) and Chem. Abstr. 57, 11239 (1962)].

The examples given hereinafter are deemed to illustrate the invention in a more detailed manner.

EXAMPLE 1

A commercial detergent powder having a neutral odour was perfumed with methyl 2,6,6-trimethyl-cyclohex-2-en-1-yl carboxylate, the said ingredient being added thereto in the proportion of 0.05%.

The thus perfumed powder exhibits a pleasant fruity odour note, reminiscent of that of ripe fruits.

EXAMPLE 2

A base perfume composition was prepared as indicated hereinafter:

| Ingredients | Parts by weight |
|---|---|
| Geranylacetone | 200 |
| Benzyl salicylate | 100 |
| Ethyl acetyl-acetate | 100 |
| Phenylethyl alcohol | 80 |
| Elemol | 60 |
| α-Amyl-cinnamic aldehyde diethyl-ketal | 50 |
| Dodecyl acetate | 40 |
| Farnesol | 40 |
| Terpineol | 40 |
| EXALTEX ®(1) 10%* | 40 |
| Acetic aldehyde 10%* | 40 |
| CYCLOSIA ®(1) | 30 |
| β-Damascenone 1%* | 30 |
| Isononyl acetate | 30 |
| Dimethyl cyclohexenic aldehyde | 20 |
| trans-Hex-2-en-1-ol 10%* | 20 |
| Total | 920 |

*in diethyl phthalate
(1)origin: FIRMENICH SA, Geneva/Switzerland

The above base is characterized by a diffuse odour note of flowery-green type. By adding to 92 parts of the said base 8 parts of methyl 2,6,6-trimethyl-cyclohex-2-en-1-yl carboxylate, there is obtained a novel perfume composition possessing a typical "green-apple" odour note.

The thus obtained perfume composition is particularly well adapted e.g. for the perfuming of soaps or shampoos.

EXAMPLE 3

A base perfume composition of "rose" type was prepared as indicated hereinafter:

| Ingredients | Parts by weight |
|---|---|
| Geraniol | 250 |
| α-Isomethylionone | 150 |
| Citronellol | 150 |
| Benzyl acetate | 50 |
| CYCLOSIA ®(1) | 50 |
| Bulgarian rose oil 10%* | 50 |
| Rosinol crist. | 50 |
| α-Methyl-p-ter-butyl-hydrocinnamic aldehyde | 40 |
| Phenylethyl pivalate | 40 |
| Phenylethyl alcohol | 30 |
| EXALTEX ®(1) | 30 |
| Phenoxyethyl isobutyrate | 30 |
| Citronella oil of Java 10%* | 20 |
| Geranium oil of Africa | 20 |
| Phenylacetic aldehyde 10%* | 10 |
| β-Damascenone 10%* | 10 |
| Total | 980 |

*in diethyl phthalate
(1)origin: FIRMENICH SA, Geneva/Switzerland

The above base is characterized by a typical "red rose" odour note. By adding to 98 parts of the said base 2 parts of methyl 2,6,6-trimethyl-cyclohex-2-en-1-yl carboxylate, there is obtained a novel perfume composition the odour of which is fresher, more lifting and more elegant than that of the base. It now develops a typical "white rose" odour note.

EXAMPLE 4

A base perfume composition of "rose" type was prepared as follows:

| Ingredients | Parts by weight |
|---|---|
| Rhodinol | 270 |
| Nerol | 90 |
| Linalool | 30 |
| Terpineol | 30 |
| Phenyl ethyl alcohol | 12 |
| Terpinenol | 5 |
| Linalyl acetate | 2 |
| Citronellyl acetate | 15 |
| Geranyl acetate | 10 |
| Eugenol | 33 |
| Citral | 15 |
| Phenyl ethyl acetate | 20 |
| Rose oxide | 8 |
| Guaiacol | 30 |
| 1-Citronellal | 90 |
| Neryl acetate | 3 |
| Clove bud oil | 1 |
| Cadinene | 2 |
| Guaiene | 1 |
| Gum turpentine | 12 |
| Alpha-pinene | 1 |
| Myrcene | 5 |
| Limonene | 2 |
| p-Cymene | 1 |
| Total | 688 |

The odour of the above base becomes still more rosy after the addition of 15 parts of a 0.01% solution of β-damascenone in ethyl alcohol.

To the above mixture there were then added 30 parts of a 0.1% solution of methyl 2,6,6-trimethyl-cyclohex-2-en-1-yl carboxylate in ethyl alcohol. The resulting perfume composition develops a much richer and brighter rosy and fruity odour note than that of the above mixture.

EXAMPLE 5

To 688 parts of the base composition of Example 4, there were added 15 parts of a 0.01% solution of β-damascone in ethyl alcohol. There was thus obtained a new base composition having a pleasant, fresh and lifting rody odour.

The addition to the above mixture of 30 parts of a 0.1% solution of methyl 2,6,6-trimethyl-cyclohex-2-en-1-yl carboxylate in ethyl alcohol reinforces the characteristic fresh, fruity and lifting odour effect of β-damascone.

EXAMPLE 6

100 g of talcum powder were perfumed, in the proportions of 0.15% with a 50:50 mixture of β-damascone and methyl 2,6,6-trimethyl-cyclohex-2-en-1-yl carboxylate. There is thus obtained a perfumed powder having a pleasant rosy, fruity and fresh odour.

Analogous olfactive effects were achieved by making use of 50:50 mixtures of α-damascone, or β-damascenone with methyl 2,6,6-trimethyl-cyclohex-2-en-1-yl carboxylate.

EXAMPLE 7

100 g of a concentrated liquid detergent were perfumed, in the proportions of 0.15% with a 1:10 mixture of β-damascenone and methyl 2,6,6-trimethyl-cyclohex-2-en-1-yl carboxylate. There is thus obtained a liquid detergent having a particularly pleasant, rosy and fruity odour.

Analogous olfactive effects were achieved by making use of 1:10 mixtures of α-damascone, or β-damascone with methyl 2,6,6-trimethyl-cyclohex-2-en-1-yl carboxylate.

What we claim is:

1. A method for modifying, enhancing or improving the odour properties of perfumes or perfumed articles, which comprises adding thereto a small but olfactively effective amount of methyl 2,6,6-trimethyl-cyclohex-2-en-1-yl carboxylate, said compound exhibiting an original fruity-floral odour characterized by nuances of citrus type.

2. Method according to claim 1 wherein methyl 2,6,6-trimethyl-cyclohex-2-en-1-yl carboxylate is used alone or in combination with at least one additional perfuming ingredient, a diluent or a carrier.

3. A method according to claim 1 wherein methyl 2,6,6-trimethyl-cyclohex-2-en-1-yl carboxylate is used in combination with at least one additional perfuming ingredient, selected from the group consisting of α-damascone, β-damascone, γ-damascone, -δ-damascone, ε-damascone, α-damascenone, β-damascenone, γ-damascenone and δ-damascenone, in a weight ratio of approximately 20:1 to 1:20.

4. A perfume composition, which contains methyl 2,6,6-trimethyl-cyclohex-2-en-1-yl carboxylate as its olfactively active ingredient, said ingredient exhibiting an original fruity-floral odour characterized by nuances of citrus type.

5. A perfume composition according to claim 4, which contains methyl 2,6,6-trimethyl-cyclohex-2-en-1-yl carboxylate in combination with at least one additional perfuming ingredient selected from the group consisting of α-damascone, β-damascone, γ-damascone, δ-damascone, ε-damascone, α-damascenone, β-damascenone, γ-damascenone and δ-damascenone, in a weight ratio of approximately 20:1 to 1:20.

6. A perfumed article, which contains methyl 2,6,6-trimethyl-cyclohex-2-en-1-yl carboxylate as its olfactively active ingredient, said ingredient exhibiting an original fruity-floral odour characterized by nuances of citrus type.

7. A perfumed article according to claim 6, which contains methyl 2,6,6-trimethyl-cyclohex-2-en-1-yl carboxylate in combination with at least one additional perfuming ingredient selected from the group consisting of α-damascone, β-damascone, γ-damascone, δ-damascone, ε-damascone, α-damascenone, β-damascenone, γ-damascenone and δ-damascenone, in a weight ratio of approximately 20:1 to 1:20.

* * * * *